US009823280B2

(12) United States Patent
Julicher (10) Patent No.: US 9,823,280 B2
(45) Date of Patent: Nov. 21, 2017

(54) CURRENT SENSING WITH INTERNAL ADC CAPACITOR

(71) Applicant: Microchip Technology Incorporated, Chandler, AZ (US)

(72) Inventor: Joseph Julicher, Maricopa, AZ (US)

(73) Assignee: MICROCHIP TECHNOLOGY INCORPORATED, Chandler, AZ (US)

( * ) Notice: Subject to any disclaimer, the term of this patent is extended or adjusted under 35 U.S.C. 154(b) by 0 days.

(21) Appl. No.: 13/709,399

(22) Filed: Dec. 10, 2012

(65) Prior Publication Data

US 2013/0162269 A1    Jun. 27, 2013

Related U.S. Application Data

(60) Provisional application No. 61/578,502, filed on Dec. 21, 2011.

(51) Int. Cl.
| | | |
|---|---|---|
| *G01R 19/25* | (2006.01) | |
| *G08B 17/103* | (2006.01) | |
| *G01N 21/53* | (2006.01) | |
| *G08B 29/24* | (2006.01) | |

(52) U.S. Cl.
CPC ............ *G01R 19/25* (2013.01); *G01N 21/53* (2013.01); *G08B 17/103* (2013.01); *G08B 29/24* (2013.01)

(58) Field of Classification Search
CPC   G01R 27/2605; G01R 19/25; G01R 31/3177; G01R 35/005
USPC ........ 324/658, 686, 679, 603, 672; 340/628, 340/579
See application file for complete search history.

(56) References Cited

U.S. PATENT DOCUMENTS

| | | | |
|---|---|---|---|
| 3,295,121 A | 12/1966 | Scheel | 340/629 |
| 3,735,138 A | 5/1973 | Rork et al. | 250/375 |
| 3,832,678 A | 8/1974 | Gysell et al. | 340/587 |
| 4,213,047 A | 7/1980 | Mccord | 250/381 |

(Continued)

FOREIGN PATENT DOCUMENTS

| | | | |
|---|---|---|---|
| CN | 1087739 A | 6/1994 | G08B 17/11 |
| CN | 2694395 Y | 4/2005 | G08B 19/00 |

(Continued)

OTHER PUBLICATIONS

CMOS Ionization Smoke Detector ASIC with Interconnect, Timer Mode and Alarm Memory, RE46C162/163, Published Mar. 2010.*

(Continued)

*Primary Examiner* — Huy Q Phan
*Assistant Examiner* — Adam Clarke
(74) *Attorney, Agent, or Firm* — Slayden Grubert Beard PLLC (57) ABSTRACT

External conditions, e.g., smoke, temperature, humidity, humidity, pressure, flow rate, etc., affects a sensor's characteristics, wherein the sensor provides a current output representative of its characteristics as affected by the external conditions. The current output of the sensor is coupled to a sample and hold capacitor for a precision time period thereby charging the sample and hold capacitor to a voltage proportional to current provided by the sensor over the precision time period. The voltage on the sample and hold capacitor is converted to a digital representation and a determination is made whether the external condition represents an alarm situation, e.g., smoke detected from a fire.

27 Claims, 7 Drawing Sheets

(56) References Cited

U.S. PATENT DOCUMENTS

| | | | | |
|---|---|---|---|---|
| 4,222,045 | A | 9/1980 | Cholin | 340/628 |
| 4,260,984 | A | 4/1981 | Honma | 340/630 |
| 4,266,220 | A | 5/1981 | Malinowski | 340/360 |
| 4,401,978 | A * | 8/1983 | Solomon | 340/628 |
| 4,538,137 | A | 8/1985 | Kimura | 340/512 |
| 4,616,138 | A * | 10/1986 | Yuchi | G08B 17/10 250/554 |
| 4,652,866 | A | 3/1987 | Siegmann et al. | 340/628 |
| 4,672,324 | A * | 6/1987 | van Kampen | F23N 5/123 307/653 |
| 4,740,862 | A | 4/1988 | Halleck | 361/231 |
| 4,864,141 | A | 9/1989 | Lewiner | 250/381 |
| 5,173,683 | A * | 12/1992 | Brighenti et al. | 340/505 |
| 5,243,330 | A | 9/1993 | Thuillard | 340/629 |
| 5,422,807 | A | 6/1995 | Mitra et al. | 700/79 |
| 5,633,591 | A | 5/1997 | Childress et al. | 324/399 |
| 5,705,988 | A | 1/1998 | Mcmaster | 340/628 |
| 5,966,078 | A | 10/1999 | Tanguay | 340/636.1 |
| 6,257,049 | B1 | 7/2001 | Greybush | 73/29.01 |
| 6,433,712 | B1 | 8/2002 | Ohnhaeuser et al. | 341/118 |
| 6,522,254 | B1 | 2/2003 | Yamano | 340/630 |
| 6,661,346 | B1 | 12/2003 | Wood et al. | 340/601 |
| 6,981,090 | B1 | 12/2005 | Kutz et al. | 710/317 |
| 7,288,946 | B2 | 10/2007 | Hargreaves et al. | 324/678 |
| 7,307,485 | B1 | 12/2007 | Snyder et al. | 331/150 |
| 7,382,140 | B2 | 6/2008 | Obrecht | 324/678 |
| 7,460,441 | B2 | 12/2008 | Bartling | 368/118 |
| 7,521,942 | B2 | 4/2009 | Reynolds | 324/688 |
| 7,764,213 | B2 | 7/2010 | Bartling et al. | 341/152 |
| 7,834,773 | B2 | 11/2010 | Kato | 340/630 |
| 8,031,094 | B2 | 10/2011 | Hotelling et al. | 341/143 |
| 8,155,903 | B2 * | 4/2012 | Weber | G01D 5/24 702/186 |
| 8,193,822 | B2 | 6/2012 | Welland | 324/686 |
| 8,487,655 | B1 | 7/2013 | Kutz et al. | 326/86 |
| 8,510,068 | B2 | 8/2013 | Kawashima | 702/87 |
| 8,547,135 | B1 | 10/2013 | Yarlagadda et al. | 326/38 |
| 8,658,958 | B2 | 2/2014 | Lan et al. | 250/214 A |
| 8,659,694 | B2 | 2/2014 | Compton et al. | 348/308 |
| 8,780,068 | B2 | 7/2014 | Lin | 345/173 |
| 8,884,771 | B2 | 11/2014 | Cooke et al. | 340/628 |
| 8,981,754 | B1 | 3/2015 | Rohilla et al. | 323/312 |
| 9,035,243 | B2 | 5/2015 | Lenkeit et al. | 250/287 |
| 9,367,179 | B2 | 6/2016 | Irkliy | G06F 3/044 |
| 2002/0078744 | A1* | 6/2002 | Gehman et al. | 73/204.11 |
| 2002/0101345 | A1* | 8/2002 | Pattok et al. | 340/516 |
| 2002/0153923 | A1 | 10/2002 | Piasecki et al. | 326/57 |
| 2003/0058114 | A1* | 3/2003 | Miller et al. | 340/577 |
| 2004/0257235 | A1 | 12/2004 | Right et al. | 340/628 |
| 2005/0030172 | A1 | 2/2005 | Right et al. | 340/521 |
| 2006/0284639 | A1 | 12/2006 | Reynolds | 324/658 |
| 2007/0019361 | A1* | 1/2007 | Obrecht | F23N 5/123 361/247 |
| 2007/0075710 | A1 | 4/2007 | Hargreaves et al. | 324/658 |
| 2008/0012715 | A1* | 1/2008 | Montgomery | 340/579 |
| 2008/0079734 | A1 | 4/2008 | Leung et al. | 257/734 |
| 2008/0111714 | A1 | 5/2008 | Kremin | 341/33 |
| 2008/0169826 | A1 | 7/2008 | Bartling | 324/658 |
| 2008/0272826 | A1 | 11/2008 | Smit et al. | 327/509 |
| 2008/0312857 | A1 | 12/2008 | Sequine | 702/65 |
| 2009/0230305 | A1 | 9/2009 | Burke et al. | 250/336.1 |
| 2009/0256817 | A1 | 10/2009 | Perlin et al. | 345/174 |
| 2010/0052700 | A1 | 3/2010 | Yano et al. | 324/658 |
| 2010/0059295 | A1 | 3/2010 | Hotelling et al. | 178/18.06 |
| 2010/0060593 | A1 | 3/2010 | Krah | 345/173 |
| 2010/0097015 | A1 | 4/2010 | Knoedgen et al. | 318/135 |
| 2010/0102832 | A1 | 4/2010 | Bartling et al. | 324/679 |
| 2010/0181180 | A1 | 7/2010 | Peter | 200/5 R |
| 2010/0231241 | A1 | 9/2010 | Mueck et al. | 324/686 |
| 2010/0267309 | A1 | 10/2010 | Hyland | 446/188 |
| 2010/0283760 | A1 | 11/2010 | Leung et al. | 345/174 |
| 2010/0287571 | A1 | 11/2010 | Mohammed et al. | 719/328 |
| 2010/0295555 | A1 | 11/2010 | Emanuel et al. | 324/601 |
| 2011/0007028 | A1 | 1/2011 | Curtis et al. | 345/174 |
| 2011/0163872 | A1 | 7/2011 | Pasveer et al. | 340/539.12 |
| 2011/0234417 | A1* | 9/2011 | Aleman et al. | 340/660 |
| 2011/0267287 | A1 | 11/2011 | Bartling et al. | 345/173 |
| 2011/0267309 | A1 | 11/2011 | Hanauer et al. | 345/174 |
| 2012/0005693 | A1 | 1/2012 | Mohammed et al. | 719/328 |
| 2012/0098686 | A1* | 4/2012 | Wang | 341/118 |
| 2012/0112728 | A1 | 5/2012 | Bodo et al. | 323/311 |
| 2013/0088246 | A1 | 4/2013 | Lundstrum et al. | 324/686 |
| 2013/0090873 | A1 | 4/2013 | Lundstrum et al. | 702/64 |
| 2013/0126715 | A1* | 5/2013 | Flaherty | 250/214 R |
| 2013/0298100 | A1 | 11/2013 | Hastings et al. | 716/126 |
| 2013/0322439 | A1 | 12/2013 | Verhollen et al. | 370/389 |
| 2015/0269821 | A1* | 9/2015 | Haynes | G08B 17/10 340/532 |

FOREIGN PATENT DOCUMENTS

| | | | | |
|---|---|---|---|---|
| CN | 101213461 | A | 7/2008 | G01R 27/26 |
| CN | 101261225 | A | 9/2008 | G01N 21/53 |
| CN | 101833044 | A | 9/2010 | G01R 27/26 |
| CN | 102063774 | A | 5/2011 | G08B 17/10 |
| CN | 102096978 | A | 6/2011 | G08B 17/107 |
| CN | 102257543 | A | 11/2011 | G08B 11/00 |
| DE | 10357371 | A1 | 7/2005 | G08B 17/00 |
| DE | 102009030495 | A1 | 1/2011 | G01B 7/00 |
| EP | 0646791 | B1 | 9/2001 | G01N 33/00 |
| EP | 1719947 | A1 | 11/2006 | F23N 5/12 |
| FR | 2473201 | A1 | 7/1981 | G08B 17/11 |
| GB | 1598821 | A | 9/1981 | G08B 17/11 |
| GB | 2117560 | A | 10/1983 | G01N 27/64 |
| GB | 2156126 | A | 10/1985 | G08B 17/00 |
| JP | 6345666 | A | 2/1988 | G05B 15/02 |
| JP | 1180258 | A | 3/1999 | A61J 1/05 |
| JP | 2000049608 | A | 2/2000 | H03M 1/38 |
| JP | 2000278131 | A | 10/2000 | G06F 3/05 |
| JP | 2001223586 | A | 8/2001 | G11C 27/02 |
| JP | 3111998 | U | 7/2005 | B24D 5/00 |
| JP | 2005301974 | A | 10/2005 | G06F 3/03 |
| JP | 2008542760 | A | 11/2008 | G01R 27/26 |
| JP | 2010061405 | A | 3/2010 | G06F 3/041 |
| JP | 2010078392 | A | 4/2010 | G01N 27/70 |
| JP | 2010191834 | A | 9/2010 | G06F 3/041 |
| JP | 2010250522 | A | 11/2010 | G06F 3/041 |
| JP | 2010272991 | A | 12/2010 | G01B 7/00 |
| JP | 2011175451 | A | 9/2011 | G06F 3/041 |
| TW | 557356 | B | 10/2003 | B24B 49/00 |
| TW | 201005615 | A | 2/2010 | G06F 3/044 |
| TW | M384374 | U | 7/2010 | F21S 9/02 |
| TW | 201037287 | A | 10/2010 | G01J 1/44 |
| TW | 201041305 | A | 11/2010 | H03K 17/955 |
| TW | M400055 | U | 3/2011 | |
| TW | 201136302 | A | 10/2011 | H04N 5/335 |
| WO | 2006/138205 | A1 | 12/2006 | H03M 1/06 |
| WO | 2013/052618 | A1 | 4/2013 | H03K 17/96 |
| WO | 2013/052722 | A1 | 4/2013 | G06F 3/044 |

OTHER PUBLICATIONS

International Search Report and Written Opinion, Application No. PCT/US2013/052956, 12 pages, dated Jan. 28, 2014.

Yair, R., "Charge Sampling Method for Low Current Measurement," Review of Scientific Instruments, vol. 45, No. 3, 6 pages, Mar. 1974.

Margarita, Andrey, "Application Note AN2245: Smart Smoke Detector," Cypress Semiconductor Corporation, XP055054690, URL: http://www.psocdeveloper.com/uploads/tx_piapappnote/an2245_01.pdf, 12 pages, Feb. 22, 2005.

Perme, Thomas, "AN1101: Introduction to Capacitive Sensing," Microchip Technology, Inc., AP002693941, URL: http://ww1.microchip.com/downloads/en/AppNotes/01101A.pdf, 10 pages, Jun. 25, 2007.

Bohn, Bruce, "AN1250: Microchip CTMU for Capacitive Touch Applications," Microchip Technology, Inc., XP055007432, URL: http://www.microchip.com/stellent/idcplg?IdcService=SS_GET_PAGE&nodeID=1824&appnote=en539441, 22 pages, Feb. 3, 2009.

Perme, Thomas et al., AN1298: Capacitive Touch Using Only an ADC ("CVD"), Microchip Technology, Inc., XP055007357, URL:

(56) References Cited

OTHER PUBLICATIONS http://www.microchip.com/stellent/idcplg?IdcService=SS_GET_PAGE&nodeId=1824&appnote=en545264, 4 pages, Oct. 7, 2009.
Davison, Burke, "AN1334: Techniques for Robust Touch Sensing Design," Microchip Technology, Inc., XP055047201, URL: http://www.microchip.com/downloads/en/AppNotes/01334A.pdf, 28 pages, Aug. 6, 2010.
Yedamale, Padmaraja et al., "AN1375: See What You Can Do with the CTMU," Microchip Technology, Inc., XP055047211, URL: http://www.microchip.com/downloads/en/AppNotes/CTMU%2001375a.pdf, 12 pages, May 11, 2011.
Anonymous, "Delta-Sigma Modulation," Wikipedia, URL: http://en.wikipedia.org/w/index.php?title=Special:Book&bookcmd=download&collection_id=fa136df1282a073a&writer=rl&return_to=Delta-sigma modulation, 14 pages, 2012.
International Search Report and Written Opinion, Application No. PCT/US2012/058682, 12 pages, dated Dec. 17, 2012.
International Search Report and Written Opinion, Application No. PCT/US2012/058691, 13 pages, dated Dec. 19, 2012.
International Search Report and Written Opinion, Application No. PCT/US2012/058832, 11 pages, dated Jan. 22, 2013.
International Search Report and Written Opinion, Application No. PCT/US2012/058837, 14 pages, dated Feb. 18, 2013.
International Search Report and Written Opinion, Application No. PCT/US2012/058716, 10 pages, dated Mar. 15, 2013.
International Search Report and Written Opinion, Application No. PCT/US2012/069086, 10 pages, dated Apr. 5, 2013.
International Search Report and Written Opinion, Application No. PCT/US2012/069094, 12 pages, dated Apr. 5, 2013.
International Search Report and Written Opinion, Application No. PCT/US2012/058688, 11 pages, dated Apr. 5, 2013.
International Search Report and Written Opinion, Application No. PCT/US2012/069076, 11 pages, dated Apr. 10, 2013.
International Search Report and Written Opinion, Application No. PCT/US2012/070466, 13 pages, dated Apr. 24, 2013.
Cuilan, Tan, Research & Design of Wireless Smoke Detection System, Engineering Science and technology II, China Master's Theses (Chinese language), 1 page (English abstract), Sep. 15, 2009.
Chinese Office Action, Application No. 201280068100.7, 5 pages, dated Oct. 9, 2015.
Chinese Office Action, Application No. 201280067196.5, 13 pages, dated Oct. 28, 2015.
U.S. Non-Final Office Action, U.S. Appl. No. 13/633,429, 21 pages, dated Jan. 8, 2016.
Japanese Office Action, Application No. 2014534713, 7 pages, dated Jun. 10, 2016.
Taiwan Office Action, Application No. 101137033, 3 pages, dated Jul. 13, 2016.
Taiwan Office Action, Application No. 101136986, 3 pages, dated Jul. 13, 2016.
Taiwan Office Action, Application No. 101136994, 3 pages, dated Jul. 13, 2016.
Japanese Office Action, Application No. 2014534704, 9 pages, dated Jul. 29, 2016.
Chinese Office Action, Application No. 201280054576.5, 5 pages, dated Mar. 31, 2016.
Chinese Office Action, Application No. 201280058691.X, 7 pages, dated Apr. 1, 2016.
Japanese Office Action, Application No. 2014534700, 8 pages, dated Apr. 20, 2016.
Chinese Office Action, Application No. 201280059635.8, 8 pages, dated Jun. 3, 2016.
Chinese Office Action, Application No. 201280068100.7, 4 pages, dated Jun. 13, 2016.
Chinese Office Action, Application No. 201280056484.0, 4 pages, dated Jun. 15, 2016.
Taiwan Office Action, Application No. 101149173, 8 pages, dated Jun. 21, 2016.
Japanese Office Action, Application No. 2014534704, 2 pages, dated Jan. 27, 2017.
Chinese Office Action, Applicatio No. 201280054576.5, 4 pages, dated Feb. 7, 2017.
Japanese Final Office Action, Application No. 2014-534700, 5 pages, dated Mar. 2, 2017.
U.S. Notice of Allowance, U.S. Appl. No. 14/967,930, 57 pages, dated Jun. 29, 2017.
European Office Action, Application No. 12783423.2, 7 pages, dated Jun. 22, 2017.
Chinese Office Action, Application No. 201280067196.5, 25 pages, dated Sep. 6, 2016.
Taiwan Notice of Allowance, Application No. 101147651, 4 pages, dated Jan. 11, 2017.
European Office Action, Application No. 12783424.0, 5 pages, dated May 24, 2017.
European Office Action, Application No. 12798040.7, 7 pages, dated May 24, 2017.
Japanese Office Action, Application No. 2014534703, 5 pages, dated Dec. 22, 2016.
Chinese Office Action, Application No. 201280058691.X, 9 pages, dated Nov. 15, 2016.
Taiwan Office Action, Application No. 101147653, 3 pages, dated Nov. 17, 2016.

\* cited by examiner

CURRENT SENSING WITH INTERNAL ADC CAPACITOR

RELATED PATENT APPLICATION

This application claims priority to commonly owned U.S. Provisional Patent Application Ser. No. 61/578,502; filed Dec. 21, 2011; entitled "Current/Voltage Interface," by Joseph Julicher; which is hereby incorporated by reference herein for all purposes.

TECHNICAL FIELD

The present disclosure relates to a sensor interface, and, in particular, for a microcontroller having a current input interface using an internal sampling capacitor, timer and analog-to-digital converter.

BACKGROUND

Some sensors such as the photo transistors produce a current which needs to be converted into a digital value. Conventional photo smoke sensors require external circuitry to handle the often very small output currents therefrom. For example, present technology photo smoke detectors use high speed amplifiers to detect the light change in the smoke chamber. A current technology interface for a current to voltage conversion use transconductance amplifiers which require an operational amplifier. Operational amplifiers may also be used to control the excitation current for a light emitting diode (LED) in a smoke detection photo chamber.

There are three types of smoke detectors available today: (1) photoelectric, (2) ionization, and (3) a combination of photoelectric and ionization that have both types of sensors. A photoelectric alarm is triggered when smoke detected based upon the amount of light detected from a light source onto a light sensor. In an ion smoke detector, ionized air molecules attach to the smoke particles that enter the chamber, reducing the ionizing current and triggering the smoke alarm detection circuits.

The ion detector reacts faster than the photoelectric detector in responding to flaming fires, and the photoelectric detector is more responsive to smoldering fires. Because an ion detector tests the air for small combustible particles, it can be fooled by chemical or paint particles in the atmosphere. The photoelectric detector, which needs to "see" the smoke from the fire, can be fooled by dust, steam or even spider webs. Though both offer protection against undetected fires, ion detectors experience a higher incidence of nuisance alarms.

Optical beam smoke detectors work on the principle of light obscuration, where the presence of smoke blocks some of the light from the light source beam. Once a certain percentage of the transmitted light has been blocked by the smoke, a fire alarm is generated. Optical beam smoke detectors are typically used to detect fires in large commercial and industrial buildings, as components in a larger fire alarm system.

Optical beam smoke detectors consist of at least one light transmitter and one receiver, which is photosensitive. The photosensitive receiver monitors light produced by the transmitter under normal conditions. In the absence of smoke, light passes from the light transmitter to the receiver in a straight line. In a fire, when smoke falls within the path of the beam detector, some of the light is absorbed or scattered by the smoke particles. This creates a decrease in the received light signal, leading to an increase in optical obscuration i.e. a reduction of transmittance of light across the beam path.

It would be desirable to improve the reliability, lower the power consumption and reduce manufacturing costs of fire alarms using photo optical smoke detectors.

SUMMARY

Therefore there is a need for an improved current interface to an external sensor having a current out, and in particular integrated within a microcontroller.

According to an embodiment, a system for measuring a current may comprise: a current source; and a microcontroller having at least one external port pin directly connected with the current source, the microcontroller comprising: an analog-to digital converter (ADC); a sample and hold capacitor associated with the ADC; a timer; a first switch coupling between the sample and hold capacitor and the external port pin, and controlled by the timer; and a second switch coupled to the sample and hold capacitor, wherein the second switch may be adapted for discharging the sample and hold capacitor.

According to a further embodiment, the microcontroller may comprises a control unit for controlling said ADC, timer, and said second switch. According to a further embodiment, the control unit may be a state machine. According to a further embodiment, the control unit may be configured to control the second switch to discharge the sample capacitor and after the capacitor has been discharged, to control the second switch to be opened and the first switch to be closed, and after a predetermined time period to control the first switch to be opened and an analog-to-digital conversion started by the ADC. According to a further embodiment, the current source may be an optical photo detector excited by a light source.

According to a further embodiment, the optical photo detector detects smoke from a fire when a light level detected from the light source changes due to the smoke. According to a further embodiment, the current source may be selected from the group consisting of a resistance temperature detector (RTD), a humidity detector, a pressure transducer, and a flow rate transducer. According to a further embodiment, the light source and optical photo detector may be periodically turned on by the microcontroller for conserving power thereto.

According to another embodiment, a system for measuring a current may comprise: a current source; and a microcontroller having at least one external port pin directly connected with the current source, the microcontroller may comprise: an analog-to digital converter (ADC); a sample and hold capacitor associated with the ADC; a timer having an output for providing a voltage pulse to the current source for a defined period of time; a first switch coupled to the sample and hold capacitor, wherein the first switch may be adapted for discharging the sample and hold capacitor; and a second switch for coupling the sample and hold capacitor to the ADC for conversion of a voltage on the sample and hold capacitor to a digital representation thereof.

According to yet another embodiment, an integrated circuit device for determining a process variable based upon a process sensor having a current output may comprise: a capacitor having a known capacitance value; a timer generating a time period of known value; an analog-to-digital converter (ADC); and a digital processor having a memory, the digital processor may be coupled to the timer and the ADC, wherein the known value capacitor coupled to the current output of the process sensor and begins charging with the current from the process sensor upon a start signal from the timer, the known value capacitor may be decoupled from the current output of the process sensor upon a stop signal from the timer, the ADC samples and converts a voltage on the capacitor to a digital representation thereof, and the digital processor reads from the ADC the digital representation of the voltage and determines therefrom a process value.

According to a further embodiment, the digital processor may determine whether the value of the process variable comprises an alarm condition. According to a further embodiment, the process sensor may be an optical photo detector. According to a further embodiment, the optical photo detector detects smoke from a fire. According to a further embodiment, an analog multiplexer may have a first input coupled to the optical photo detector and a second input coupled to an ionization chamber smoke detector, wherein the optical photo detector and ionization chamber smoke detector may be located within a smoke detector chamber having an opening to allow smoke to enter therein.

According to a further embodiment, a light emitting diode (LED) may be used as a light source for the optical photo detector. According to a further embodiment, the LED may be controlled by the digital processor. According to a further embodiment, a look-up table may be used for converting the digital representations into process values, wherein the look-up table may be stored in the memory. According to a further embodiment, the integrated circuit device may be a microcontroller.

According to till another embodiment, a method for measuring a current from a process sensor may comprise the steps of: shorting a capacitor to substantially zero volts; coupling the capacitor to a process sensor having a current output; charging the capacitor with the current output from the process sensor; decoupling the capacitor from the process sensor after a certain time period; converting a voltage on the capacitor to a digital representation thereof with an analog-to-digital converter (ADC); reading the digital representation from the ADC with a digital processor; and determining a process value from the digital representation with the digital processor.

According to a further embodiment of the method, the process sensor may be an optical photo detector. According to a further embodiment of the method, the optical photo detector detects smoke from a fire. According to a further embodiment of the method, the step of determining a smoke alarm condition may be determined from the process value.

According to another embodiment, a method for measuring a current from a process sensor may comprise the steps of: shorting a capacitor having a known capacitance to substantially zero volts; applying a voltage pulse having a known time period to a process sensor having a current output that may be coupled to the capacitor; charging the capacitor with the current output from the process sensor; converting a voltage on the capacitor to a digital representation thereof with an analog-to-digital converter (ADC); reading the digital representation from the ADC with a digital processor; and determining a process value from the digital representation with the digital processor.

According to a further embodiment of the method, the process sensor may be an optical photo detector. According to a further embodiment of the method, the optical photo detector detects smoke from a fire. According to a further embodiment of the method, the step of determining a smoke alarm condition may be determined from the process value.

BRIEF DESCRIPTION OF THE DRAWINGS

A more complete understanding of the present disclosure may be acquired by referring to the following description taken in conjunction with the accompanying drawings wherein.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

DETAILED DESCRIPTION

According to embodiments of this disclosure discussed herein will allow, in particular, small currents to be directly measured with a microcontroller without any external components. For example, a timed pulse may be used in place of an operational amplifier controlled linear current source. A pulse timer peripheral is already present on many microcontroller units that can provide a 65,000:1 dynamic range which will easily provide the calibration range required. The current can be captured as a charge current on an internal analog-to-digital converter (ADC) sample and hold (S/H) capacitor. The ADC can then be used to produce a digital value proportional to the current supplied to the S/H capacitor over a known precision time period.

The ADC sampling capacitor comprises certain constraints. However, these constraints are known. External solutions require additional amplification steps to combat parasitic affects of the equipment printed circuit board (PCB) and other environment conditions. By moving the necessary circuit parts inside of the microcontroller and ADC, these parasitic affects are readily known, controlled, and the circuit solution is more compact and sensitive to sensor inputs.

Such a current/voltage interface can be advantageously be used in a smoke detector and will significantly reduce the cost of interfacing to an optical photo smoke sensor. According to various embodiments, a current sourced by an external device such as a photo chamber is connected to the input of an ADC. The internal sampling capacitor of the ADC accepts the current charge and creates a voltage linearly over a fixed precision time period. After the fixed precision time period has elapsed, the voltage on the S/H capacitor may be measured by starting a conversion from analog to digital with the ADC.

Portions of a Charge Time Measurement Unit (CTMU) may be used in determining the voltage charge value on the S/H capacitor. The CTMU is more fully described in Microchip applications notes AN1250, AN1375, etc., available at www.microchip.com, and U.S. Pat. Nos. 7,460,441 B2 and 7,764,213 B2; wherein all are hereby incorporated by reference herein for all purposes. The CTMU voltage charge measurement accuracy is achieved by charging a known value capacitor from a current source over a known time period, then sampling a voltage developed on the charged capacitor. This sampled voltage is then converted into a digital value with an analog-to-digital converter (ADC) and, optionally, a look-up table may be used, or other means, to convert the digital value of the sampled voltage into a value for comparison against a reference value. If the sampled voltage value is significantly different, as in an alarm condition, e.g., smoke detection, than the reference value then an alarm may be initiated. If the sampled voltage value is within desired values then no alarm condition exists.

The various embodiments described herein, provide for the ability to create a cost effective solution for applications using sensors having current outputs. Thus, the need for expensive operational amplifiers and associated circuitry is removed. An interface according to various embodiments may be advantageously used in smoke detector photo chambers to detect fast occurring smoky fires. A photo chamber consists of an LED and a Photodiode. As discussed above, the photodiodes are often measured using high speed transconductance amplifiers (15 MHz GBW), followed by low pass active filters and finally ADC or comparators according to conventional systems. Using the internal ADC capacitor eliminates external components and saves power.

Referring now to the drawings, the details of specific example embodiments are schematically illustrated. Like elements in the drawings will be represented by like numbers, and similar elements will be represented by like numbers with a different lower case letter suffix.

Figure 1:
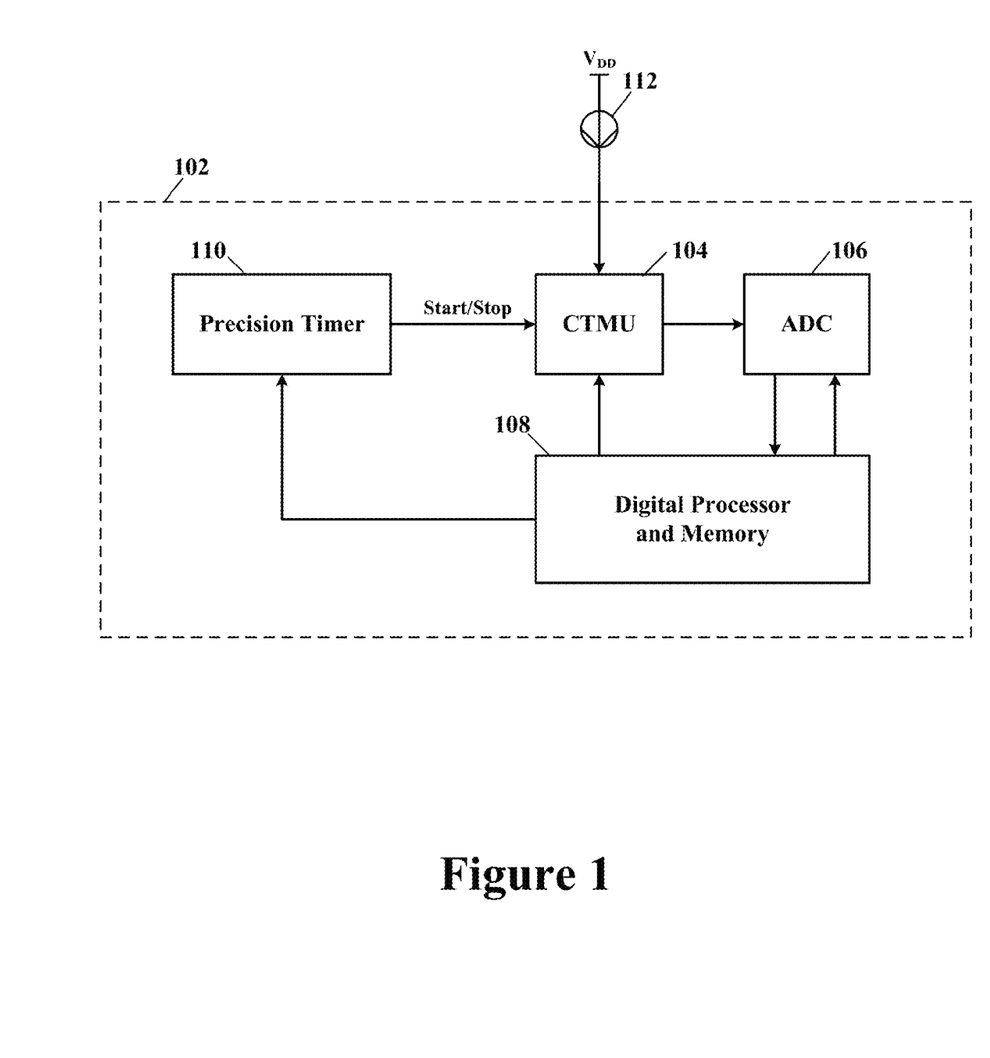
FIG. 1 illustrates a schematic block diagram of a sensor coupled to a current input interface of a microcontroller, according to a specific example embodiment of this disclosure.

Referring to FIG. 1, depicted is a schematic block diagram of a sensor 112 coupled to a current input interface of a microcontroller 102, according to a specific example embodiment of this disclosure. The microcontroller 102 may comprise a charge time measurement unit (CTMU) 104, an analog-to-digital converter (ADC) 106, a digital processor and memory 108, and a precision timer 110. All circuit functions, e.g., internal peripherals, reside in the microcontroller 102 necessary for reading (measuring) the current output of the sensor 112. The sensor 112 having a current output may be for example, but is not limited to, a photoelectric diode, a resistance temperature detector (RTD), humidity detector, pressure transducer, flow rate transducer, etc., wherein the sensor 112 supplies a current proportional to the sensed process variable, e.g., smoke, temperature, etc. A constant current source sensor will enable precise conversion of the process variable, and a current source that is non-linear may still be used to provide process measurement values that may be converted to useful information with a look-up table and/or curve fitting formulas, etc. For monitoring an alarm condition the linearity of the current source sensor is of secondary importance.

Figure 2:
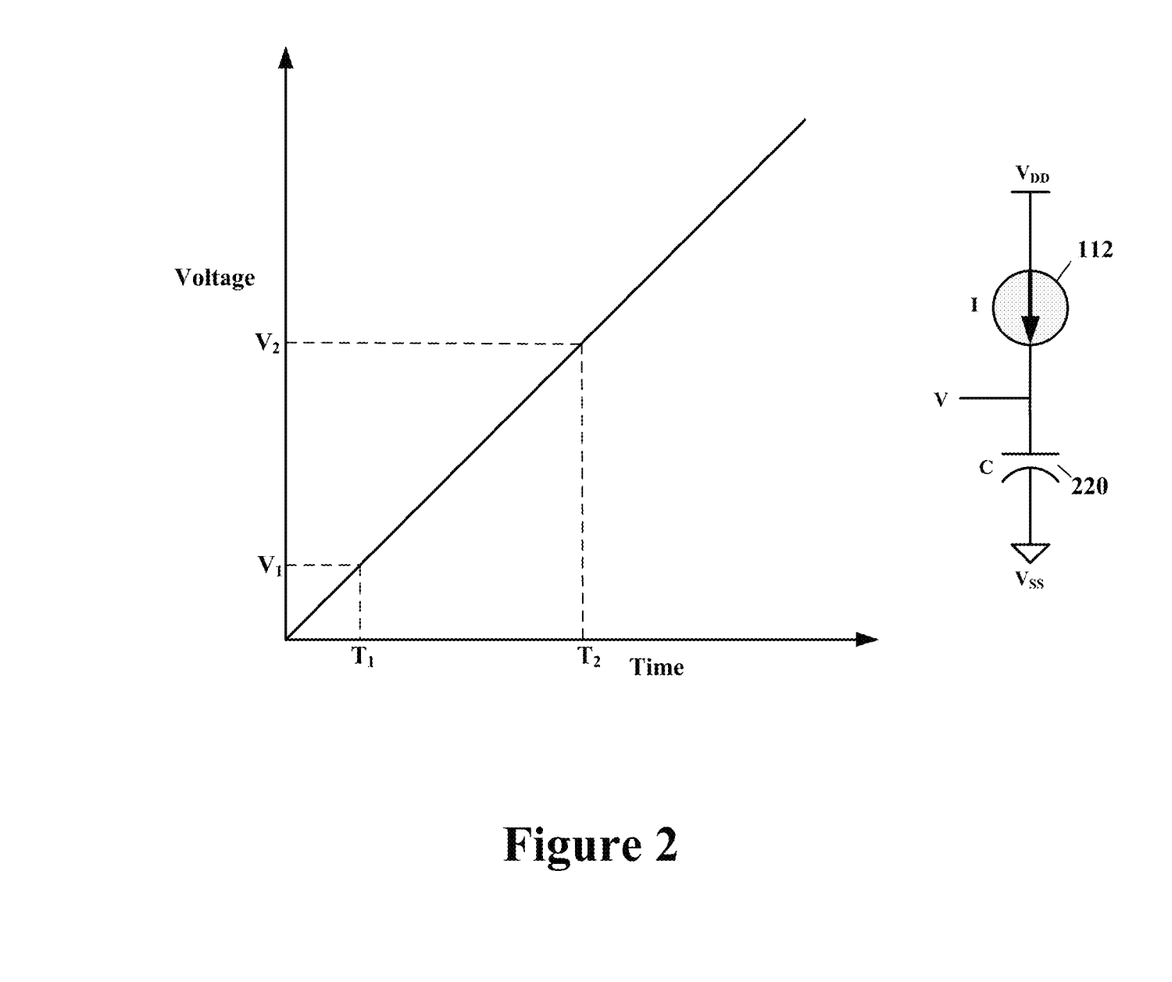
FIG. 2 illustrates a time-voltage graph of a capacitor being charged from a constant current source.

Referring to FIG. 2, depicted is a time-voltage graph of a capacitor being charged from a constant current source. When a capacitor 220 is charged through a constant current source 112 (e.g., sensor), the voltage, V, across the capacitor 220 increases linearly with time, according to equation (1):

$$I = C * dV/dT \qquad \text{Eq. (1)}$$

where C is the capacitance value of the capacitor 220, I is the current from the constant current source 112 and V is the voltage on the capacitor 220 at time T. When any two values of the current, I; time, T; and voltage, V are known, the other unknown value may be calculated from the two known values. For example, if the capacitance of the capacitor 220 and the time $T=T_2-T_1$ are known, and the voltage V on the capacitor 220 is measured, a current charge may be determined. This allows conversion of the voltage charge (e.g., voltage on the capacitor 220) to the measured process variable. A simple voltage to process variable value look-up table may also be provided and stored in the memory of the digital processor 108.

Figure 3:
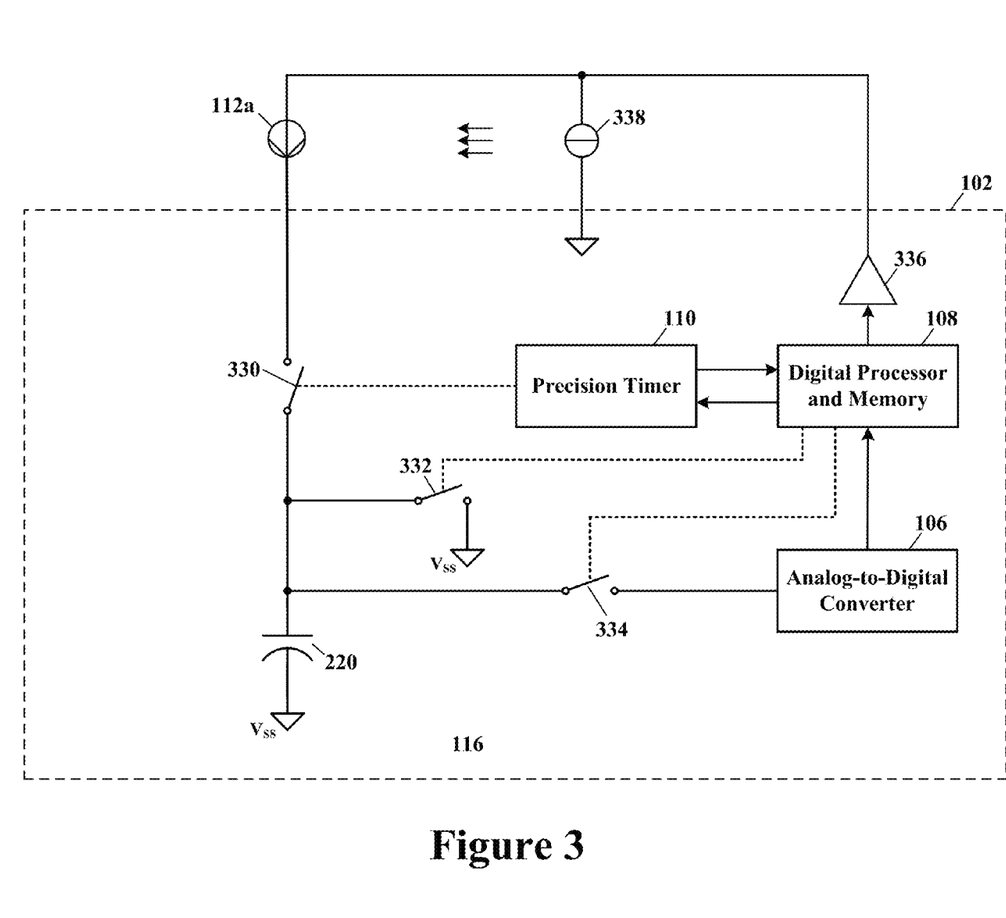
FIG. 3 illustrates a schematic block diagram of a photo-optic sensor and light source coupled to current input and output interfaces of a microcontroller, according to another specific example embodiment of this disclosure.

Referring to FIG. 3, depicted is a schematic block diagram of a photo-optic sensor and light source coupled to current input and output interfaces of a microcontroller, according to another specific example embodiment of this disclosure. The microcontroller 102 comprises an internal analog-to-digital converter (ADC) 106 having an associated sample and hold (S/H) capacitor 220. Furthermore a sample and hold switch 330 and a discharge switch 332 are provided. The discharge switch 332 discharges the S/H capacitor 220 to substantially zero (0) volts. An ADC switch 334 is provided to couple the ADC 106 to the S/H capacitor 220 during an analog-to-digital conversion cycle.

A precision timer 110 may be used to precisely control the sample and hold switch 330. A digital processor 108 may be used to control the discharge switch 332 and the ADC switch 334 (or the ADC 106 peripheral may control the switch 334) and start the precision timer 110, or an independent control unit (not shown) may be separately provided from digital processor 108 to independently control the operation of the entire CTMU peripheral in the microcontroller 102. According to other embodiments, this control unit (not shown) may be, for example, a programmable state machine or any other suitable sequential control unit within the microcontroller 102. The current source is indicated with numeral 112a and may be a sensor, for example a photo smoke detector, and a light source light emitting diode (LED) 338, both in smoke chamber (see FIG. 6). An output driver 336 may be used to turn on the light source LED 338 and supply operating voltage to the sensor 112a periodically for conservation of power, e.g., battery power.

Figure 4:
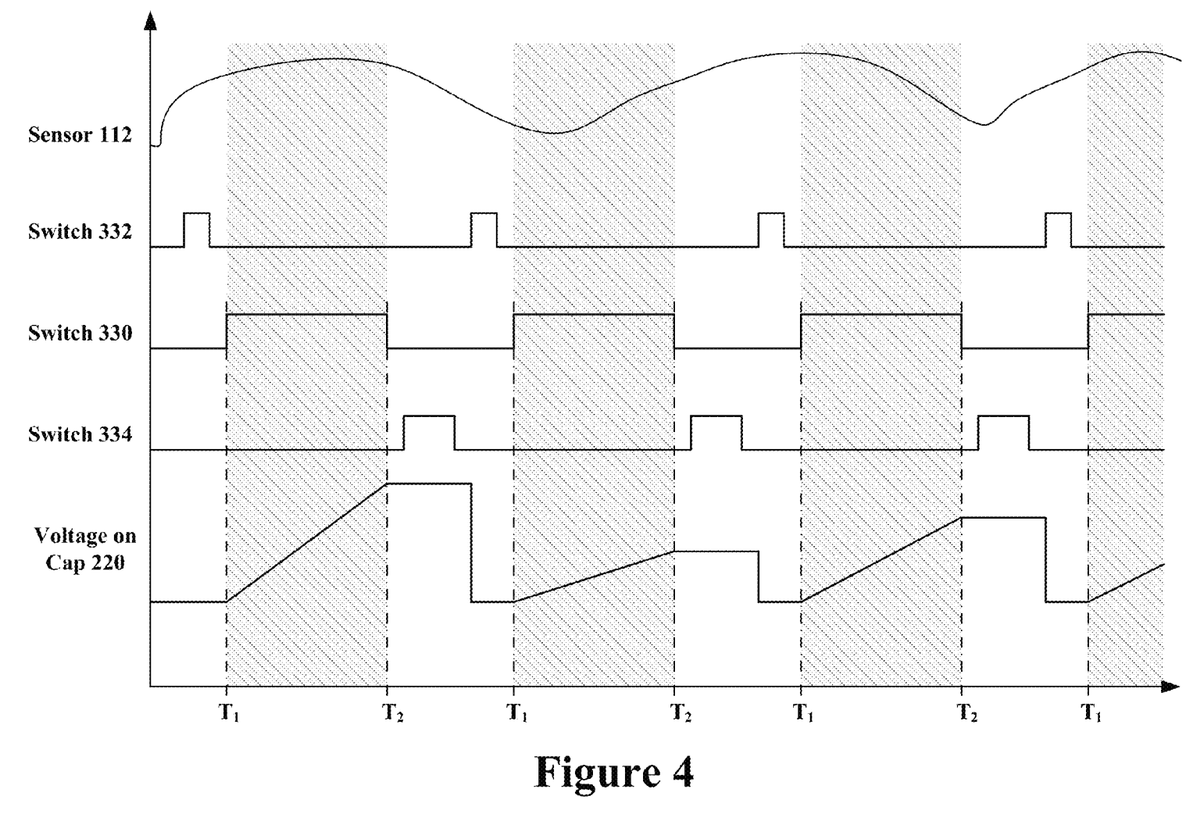
FIG. 4 illustrates schematic timing diagrams for operation of the peripheral functions shown in FIG. 3, according to the teachings of this disclosure.

Referring to FIG. 4, depicted are schematic timing diagrams for operation of the peripheral functions shown in FIG. 3, according to the teachings of this disclosure. Switch 332 closes, shorting out any charge on the S/H capacitor 220 to zero volts. Then the precision timer 110 closes the sample and hold switch 330 for a know fixed period of time, $T=T_2-T_1$. Then after time T the sample and hold switch 330 opens. This causes the sample and hold capacitor 220 to be charged at a rate determined by the current source, e.g., the current from the sensor 112. After the time period T has elapsed, the ADC switch 334 closes and the ADC 106 converts the voltage charge on the S/H capacitor 220 to a digital representation thereof. The digital processor 108 may thereafter read this digital representation for further processing, e.g., alarm notification and/or process variable representation.

Figure 5:
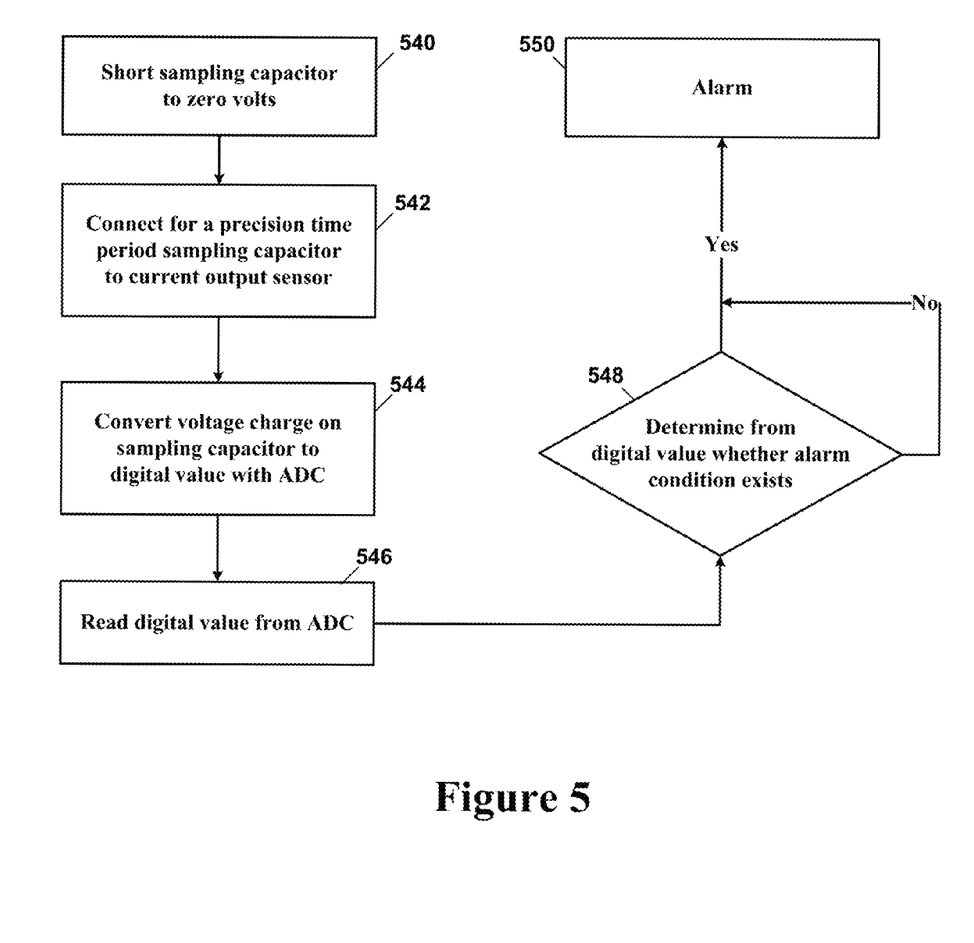
FIG. 5 illustrates a schematic process flow diagram of the operation of the circuit shown in FIG. 3, according to the teachings of this disclosure.

Referring to FIG. 5, depicted is a schematic process flow diagram of the operation of the circuit shown in FIG. 3, according to the teachings of this disclosure. In step 540 the S/H capacitor 220 is shorted to ground to remove any charge thereon to zero (0) volts. In step 542 the S/H capacitor 220 is coupled to a current source, e.g., current output sensor 112*a* for a precision time determined by, for example but not limited to, the precision timer 110. After the precision time period has elapsed, in step 544 the resultant voltage charge on the S/H capacitor 220 is converted to a digital representation by the ADC 106. In step 546 the digital representation is read by the digital processor 108. In step 548 a determination is made whether the read digital representation of the voltage charge on the S/H capacitor 220 indicates that an alarm condition exists, e.g., smoke detected. If an alarm condition has been determined in step 548, an alarm is generated in step 550.

Figure 6:
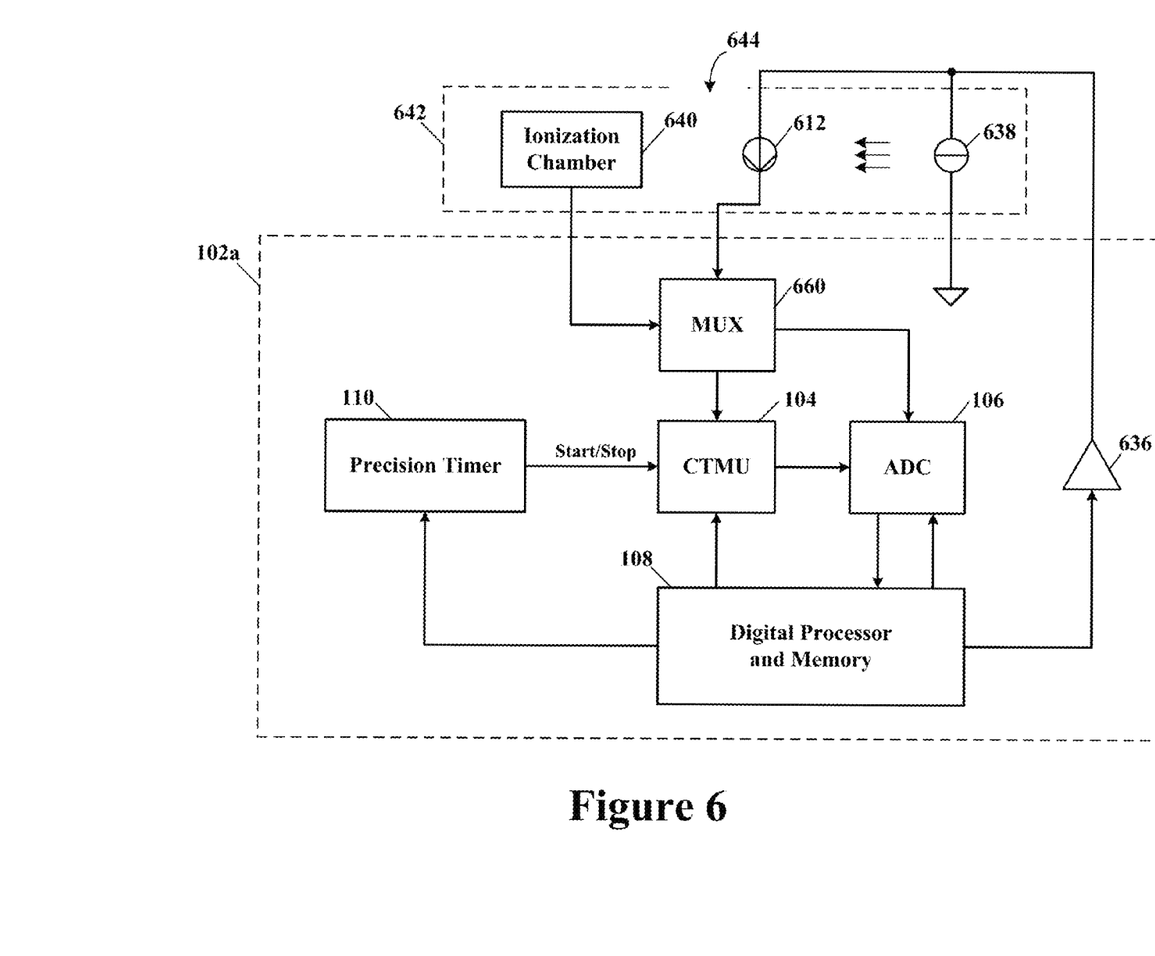
FIG. 6 illustrates a schematic block diagram of a smoke detector system using a combination of photoelectric and ionization sensors, according to yet another specific example embodiment of this disclosure.

Referring to FIG. 6, depicted is a schematic block diagram of a smoke detector system using a combination of photoelectric and ionization sensors, according to yet another specific example embodiment of this disclosure. The microcontroller 102*a* comprises a charge time measurement unit (CTMU) 104, an internal analog-to-digital converter (ADC) 106, a digital processor and memory 108, a precision timer 110, a multiplexer 660, and an output driver 636. Functionally the microcontroller 102*a* operates in substantially the same way as the microcontroller 102 shown in FIG. 3 with the addition of the multiplexer 660 that is coupled to a photo-electric smoke sensor 612, excited by a light source light emitting diode (LED) 638, and an ionization chamber smoke detector 640 located in a smoke detection chamber 642. The smoke detection chamber 642 has an opening 644 to allow smoke to enter therein. The microcontroller 102*a* shown in FIG. 6 enables a dual function smoke detector having both optical and ionization smoke detectors, and requiring only a single inexpensive integrated circuit microcontroller 102*a* for operation thereof. The constant current source of the CTMU 104 is replaced by the photo-electric smoke sensor 612

Figure 7:
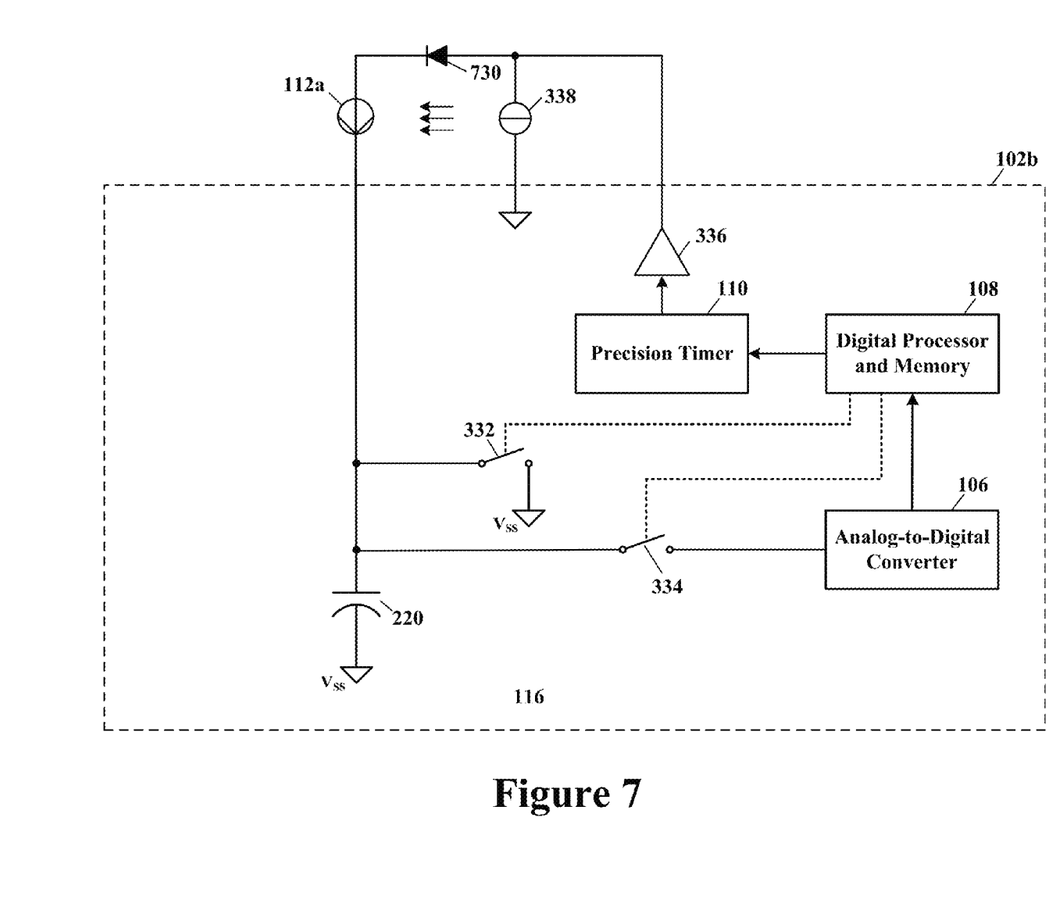
FIG. 7 illustrates a schematic block diagram of a photo-optic sensor and light source coupled to current input and output interfaces of a microcontroller, according to yet another specific example embodiment of this disclosure.

Referring to FIG. 7, depicted is a schematic block diagram of a photo-optic sensor and light source coupled to current input and output interfaces of a microcontroller, according to yet another specific example embodiment of this disclosure. The microcontroller 102*b* comprises an internal analog-to-digital converter (ADC) 106 having an associated sample and hold (S/H) capacitor 220. Furthermore a discharge switch 332 and an ADC switch 334 are provided. The discharge switch 332 discharges the S/H capacitor 220 to substantially zero (0) volts. The ADC switch 334 couples the ADC 106 to the S/H capacitor 220 during an analog-to-digital conversion cycle.

A precision timer 110 may be used to precisely control a voltage pulse to a light source 338 and a current source 112*a*. A digital processor 108 may be used to control the discharge switch 332 and the ADC switch 334 (or the ADC 106 peripheral may control the switch 334) and also start the precision timer 110, or an independent control unit (not shown) may be separately provided from digital processor 108 to independently control the operation of the entire CTMU type peripheral in the microcontroller 102*b*. According to other embodiments, this control unit (not shown) may be, for example, a programmable state machine or any other suitable sequential control unit within the microcontroller 102. The current source 112*a* may be a sensor, for example a photo smoke detector, and a light source light emitting diode (LED) 338, both in smoke chamber (see FIG. 6). An output driver 336 may be used to drive the light source LED 338 and current source 112*a* with a pulse having a pulse width of a time duration determined by the timer 110. Periodically generating the pulse will conserve power, e.g., battery power. The diode 730 prevents a voltage discharge path from the capacitor 220 through the LED 338.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A system for measuring a current, said system comprising:
   a current source; and
   a single chip microcontroller having at least one external port pin directly connected with the current source, the single chip microcontroller comprising:
      an analog-to digital converter (ADC);
      a sample and hold capacitor associated with the ADC;
      a timer;
      a first switch coupled between the sample and hold capacitor and the external port pin, and controlled by the timer;
      a second switch coupled to the sample and hold capacitor, wherein the second switch is adapted for discharging the sample and hold capacitor, and
      a control unit for controlling said ADC, timer, and said second switch, wherein the timer defines a predetermined time period during which the sample and hold capacitor is charged;
      wherein the control unit is configured to control the second switch to discharge the sample capacitor and after the capacitor has been discharged, to control the second switch to be opened and the timer to start running thereby closing the first switch, wherein the timer controls the first switch to be opened after the predetermined time period whereupon the control unit controls the ADC to start an analog-to-digital conversion converting a voltage across said sample and hold capacitor to a digital value.

2. The system according to claim 1, wherein sample and hold capacitor is associated with the ADC.

3. The system according to claim 2, wherein the control unit is a state machine.

4. The system according to claim 1, wherein sample and hold capacitor has a known value.

5. The system according to claim 1, wherein the current source is an optical photo detector excited by a light source.

6. The system according to claim 5, wherein the optical photo detector detects smoke from a fire when a light level detected from the light source changes due to the smoke.

7. The system according to claim 1, wherein the current source is selected from the group consisting of a resistance temperature detector (RTD), a humidity detector, a pressure transducer, and a flow rate transducer.

8. The system according to claim 5, wherein the light source and optical photo detector are periodically turned on by the single chip microcontroller for conserving power thereto.

9. A system for measuring a current, said system comprising:
   a current source; and
   a single chip microcontroller having at least one external port pin directly connected with the current source, the single chip microcontroller comprising:
   an analog-to digital converter (ADC);
   a sample and hold capacitor associated with the ADC;
   a timer having an output for providing a voltage pulse to the current source for a defined period of time;
   a first switch coupled to the sample and hold capacitor, wherein the first switch is adapted for discharging the sample and hold capacitor;
   a second switch for coupling the sample and hold capacitor to the ADC for conversion of a voltage on the sample and hold capacitor to a digital representation thereof, and
   a control unit for controlling said ADC, timer, and said second switch,
   wherein the control unit is configured to control the second switch to discharge the sample capacitor and after the capacitor has been discharged, to control the timer to generate the voltage pulse, wherein during the pulse duration the sample and hold capacitor is charged with a current from the current source and wherein after said defined period of time the control unit controls the second switch to couple the sample and hold capacitor to the ADC whereupon the ADC starts an analog-to-digital conversion converting a voltage across said sample and hold capacitor to a digital value.

10. A single integrated circuit device for determining a process variable based upon a process sensor having a current output, said single integrated circuit device comprising:
    at least one external port pin configured to be directly connected with the current output;
    a capacitor having a known capacitance value;
    a timer generating a time period of known value;
    an analog-to-digital converter (ADC); and
    a control unit coupled to the timer and the ADC, wherein the control unit is configured:
    to couple the known value capacitor through the at least one external port pin directly with the current output of the process sensor for a predetermined time, wherein the known value capacitor begins charging with the current from the process sensor upon a start signal from the timer,
    to decouple the known value capacitor from the current output of the process sensor upon a stop signal from the timer,
    to control the ADC to sample and convert a voltage on the capacitor to a digital representation thereof.

11. The single integrated circuit device according to claim 10, wherein the control unit is a digital processor which further determines from the digital representation a process value and whether the value of the process variable comprises an alarm condition.

12. The single integrated circuit device according to claim 10, wherein the process sensor is an optical photo detector.

13. The single integrated circuit device according to claim 12, wherein the optical photo detector detects smoke from a fire.

14. The single integrated circuit device according to claim 13, further comprising an analog multiplexer having a first input coupled to the optical photo detector and a second input coupled to an ionization chamber smoke detector, wherein the optical photo detector and ionization chamber smoke detector are located within a smoke detector chamber having an opening to allow smoke to enter therein.

15. The single integrated circuit device according to claim 12, further comprising a light emitting diode (LED) used as a light source for the optical photo detector.

16. The single integrated circuit device according to claim 15, the LED is controlled by the control unit.

17. The single integrated circuit device according to claim 10, further comprising a look-up table for converting the digital representations into process values, wherein the look-up table is stored in the memory.

18. The single integrated circuit device according to claim 10, wherein the integrated circuit device is a microcontroller comprising a digital processor.

19. A method for measuring a current from a process sensor using a single chip microcontroller, said method comprising the steps of:
    shorting a capacitor within the single chip microcontroller to substantially zero volts;
    coupling the capacitor through an external port of the single chip microcontroller directly to an external process sensor having a current output;
    charging the capacitor with the current output from the process sensor for a predetermined time period defined by a timer;
    decoupling the capacitor from the process sensor after the predefined time period;
    converting a voltage on the capacitor to a digital representation thereof with an analog-to-digital converter (ADC) within the single chip microcontroller;
    reading the digital representation from the ADC with a digital processor of the single chip microcontroller; and
    determining a process value from the digital representation with the digital processor.

20. The method according to claim 19, wherein the process sensor is an optical photo detector.

21. The method according to claim 20, wherein the optical photo detector detects smoke from a fire.

22. The method according to claim 21, further comprising the step of determining a smoke alarm condition from the process value.

23. The method according to claim 19 wherein the method is implemented within a smoke detector comprising a multiplexer connected with an ionization chamber and a photo-electric smoke sensor, the method further comprising
    controlling said multiplexer to either connect said ionization chamber or said photo-electric smoke sensor to be coupled with the capacitor.

24. A method for measuring a current from a process sensor using a single integrated circuit microcontroller, said method comprising the steps of:
    shorting a capacitor within the single integrated circuit microcontroller having a known capacitance to substantially zero volts;
    applying a voltage pulse having a known time period to a process sensor having a current output directly coupled with an external pin of the single integrated circuit microcontroller to control the current output, wherein the external pin is coupled with the capacitor;
    charging the capacitor with the current output from the process sensor for the known time period;

converting a voltage on the capacitor to a digital representation thereof with an analog-to-digital converter (ADC) of the single integrated circuit microcontroller;

reading the digital representation from the ADC with a digital processor of the single integrated circuit microcontroller; and determining a process value from the digital representation with the digital processor.

25. The method according to claim 24, wherein the process sensor is an optical photo detector.

26. The method according to claim 25, wherein the optical photo detector detects smoke from a fire.

27. The method according to claim 26, further comprising the step of determining a smoke alarm condition from the process value.

* * * * *